United States Patent [19]

Leboul et al.

[11] Patent Number: 5,849,724
[45] Date of Patent: Dec. 15, 1998

[54] MICROORGANISM OF GENUS CHRYSOSPORIUM FOR USE IN PREPARING FARNESYL TRANSFERASE INHIBITORS

[75] Inventors: Jean Leboul, Gometz la Ville; Didier Van der Pyl, Saulx les Chartreux; Jean-Jacques Debernard, Marolles en Brie, all of France

[73] Assignee: Rhone-Poulenc Rorer S.A., Antony Cedex, France

[21] Appl. No.: 894,038

[22] PCT Filed: Jan. 19, 1996

[86] PCT No.: PCT/FR96/00089

§ 371 Date: Aug. 8, 1997

§ 102(e) Date: Aug. 8, 1997

[87] PCT Pub. No.: WO96/25512

PCT Pub. Date: Aug. 22, 1996

[30] Foreign Application Priority Data

Feb. 17, 1995 [FR] France .................................. 95 01866

[51] Int. Cl.$^6$ ...................................................... A61K 31/00
[52] U.S. Cl. .......................... 514/75; 552/502; 552/506; 552/510; 552/511; 435/254.1
[58] Field of Search .............................. 514/75; 552/502, 552/506, 510, 511; 435/254.1

[56] References Cited

PUBLICATIONS van der Pyl et al., *J. Antibiot.*, 48(7), 736–7, 1995.

*Primary Examiner*—Cecilia J. Tsang
*Assistant Examiner*—C. Delacroix-Muirheid
*Attorney, Agent, or Firm*—Raymond S. Parker, III; Michael B. Martin

[57] ABSTRACT

A Chrysosporium strain No. CBS 123.95, mutants and derivatives thereof, and a method for preparing non-peptide compounds using said strain, are disclosed. Novel compounds of general formula (I), pharmaceutical compositions containing same, and the use of said compounds in anticancer treatments, are also disclosed.

12 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:1:

Cys Xaa Xaa Xaa
    1

MICROORGANISM OF GENUS CHRYSOSPORIUM FOR USE IN PREPARING FARNESYL TRANSFERASE INHIBITORS

The present invention relates to a strain of microorganism and to new compounds exhibiting farnesyl transferase-inhibiting properties.

Various genes, called proto-oncogenes and suppressor genes, are involved in the control of cell division. Among these, the ras genes and their products, generally designated Ras proteins, play a key role in the control of cell proliferation in all the eukaryotic organisms where they have been sought out. In particular, it has been shown that certain specific modifications of these proteins cause them to lose their normal control and lead them to become oncogenic. Accordingly, a large number of human tumours (about 10 to 30%) have been associated with the presence of modified ras genes.

The elucidation of the exact role of these Ras proteins in cells, the way they function and their characteristics therefore constitutes a major factor for the understanding of and the therapeutic approach to carcinogenesis.

The corresponding protein is synthesized in vivo in the form of a cytosoluble precursor and then post-translationally modified so as to confer its biological activity on it and allow it to transform mammalian cells. The first and necessary stage of these post-translational modifications consists in a farnesylation of the thiol group of a cysteine unit, located at the level of the terminal carbonyl group of Ras. This cysteine unit forms part of the identification sequence for prenylation, CAAX (SEQ ID No. 1), where C represents cysteine, A an aliphatic residue and X any amino acid. It is the protein farnesyl transferase which catalyses the transfer of a farnesyl group from farnesyl diphosphate to the compound CAAX Ras and therefore which confers, at the end of this prenylation, the required biological activity on the protein to transform cells.

The discovery of compounds inhibiting this post-translational modification has quickly emerged as one of the possible means for developing new anticancer treatments. The inhibition of the farnesylation of Ras could block the localization of the Ras protein at the membrane level and could consequently block its ability to transform normal cells into cancerous cells.

The main object of the present invention is to provide new farnesyl transferase inhibitors.

More specifically, the present invention results from the isolation of a strain of microorganism related to the genus Chrysosporium, more preferably to the species lobatum having particularly advantageous properties for the production of compounds manifesting inhibitory properties towards the protein farnesyl transferase.

One aspect of the invention therefore relates to a Chrysosporium strain characterized in that it is the microorganism Chrysosporium CBS 123.95, one of its derivatives or its mutants.

For the purpose of the present invention, derivative or mutant is understood to mean any strain obtained from the strain Chrysaosporium CBS 123.95 and capable of being used for the production of compounds according to the invention and more particularly exhibiting inhibitory properties towards the protein farnesyl transferase. In particular, such derivatives or mutants may be obtained by genetic modifications (alteration at the level of the DNA) or biochemical modifications. To this effect, various mutagenesis tools may be used, such as for example nonspecific tools:

physical agents (X-rays, ultraviolet rays and the like) or chemical agents (alkylating or bialkylating agents, intercalating agents and the like), or specific tools such as DNA-directed mutational insertion systems (transposons, retrotransposons, integrative plasmids and the like).

The fermentation by this strain on a suitable culture medium and subsequent extraction of the corresponding fermentation broth makes it possible to isolate compounds which, although having an original structure compared with conventional farnesyl transferase inhibitors, unexpectedly prove to be advantageous in this respect.

The present invention also relates to compounds capable of being obtained by fermentation by the Chrysosporium strain CBS 123.95 or one of its mutants via the extraction of a corresponding fermentation broth.

Another subject of the present invention relates to a process for the production of active metabolites according to which the Chrysosporium strain CBS 123.95 or one of its derivatives or mutants is cultured and at least one active metabolite is recovered.

The fermentation by the strain is carried out conventionally, namely on a culture medium containing the substrates necessary for the development of the said microorganism and under suitable aeration and temperature conditions. It is clear that the development of these optimum conditions for the development of the microorganism involves simple routine operations which are familiar to persons skilled in the art.

As a guide, the culture medium may comprise malt extract and agar. The fermentation is carried out preferably at a temperature greater than room temperature and more particularly of the order of 20° C. to 30° C. The pH is of the order of 7 and the medium is aerated and stirred.

At the end of the fermentation, the fermentation broth is recovered and it is extracted. This extraction is performed at an acidic pH, with the aid of a suitable organic solvent. This is preferably ethyl acetate. The organic phases are recovered, concentrated and reextracted with an aqueous solution alkalized to a pH of the order of 9. The corresponding aqueous phases are combined, reacidified and extracted with an organic solvent. The compound according to the invention is recovered by precipitation after the concentration of the corresponding organic phase. Example 1, presented below, shows in detail this procedure for isolating compounds according to the invention from a fermentation broth.

More particularly, the present invention relates to compounds of general formula I and their salts

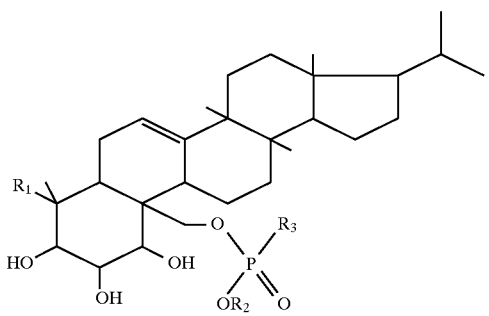

in which:
R$_1$ represents a C$_1$ to C$_5$ alkoxy group, an aldehyde group, a carboxyl group, a C$_1$ to C$_5$ alkyl ester or a (C$_1$ to C$_5$ alkyl)hydroxyl group,
R$_2$ represents a hydrogen atom or a C$_1$ to C$_4$, linear or branched, lower alkyl group, and
R$_3$ represents a C$_1$ to C$_4$ alkyl group, a hydroxyl group or a C$_1$ to C$_4$ alkoxy group.

More preferably, they are compounds of general formula II:

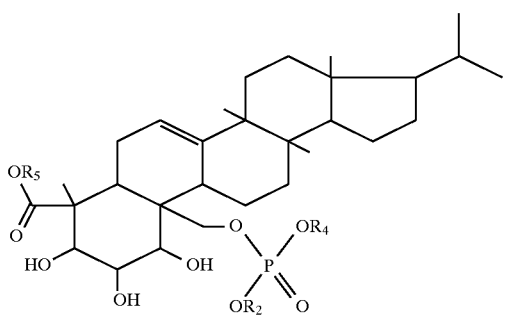

in which R$_2$ and R$_4$ correspond to the definition presented above for R$_2$ and R$_3$ represents a hydrogen atom, a C$_1$ to C$_5$ alkyl group, where appropriate substituted with a group chosen from the hydroxyl or phenyl groups, optionally substituted with one or more methyl, methoxy, hydroxyl or halogen groups.

As preferred compounds according to the invention, there may be mentioned more particularly the following compound as well as its salts:

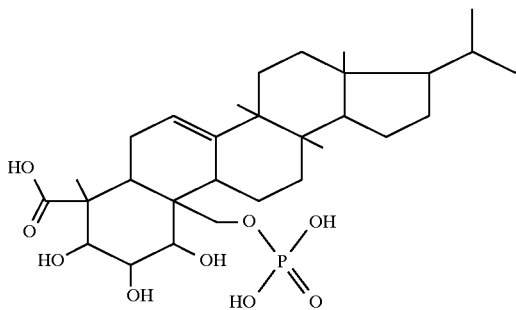

Unexpectedly, it has a significant activity in vitro in the farnesyl transferase inhibition test.

The principle of the SPA (Scintillation Proximity Assay) technology is applied to the assay of the enzymatic activity of farnesyl transferase. According to this method, the farnesyl transferase inhibiting activity is determined by the quantity of [$^3$H] farnesyl transferred from [$^3$H] farnesyl pyrophosphate, $^3$H FPP, to a biotinylated acceptor substrate.

The present invention also relates to the use of the compounds according to the invention in anticancer treatments.

It relates, in addition, to the pharmaceutical compositions containing a sufficient quantity of at least one compound according to the invention, mixed with one or more inert or physiologically active pharmaceutically acceptable adjuvants.

MATERIALS AND METHODS

A sample of the Chrysosporium strain according to the invention and which is used in the example presented below has been deposited and registered with the Centraalbureau voor Schimmel culturen (CBS) at Baarn in the Netherlands under the conditions of the Budapest treaty, under the number CBS 123.95.

Method used to detect the active metabolites: test for inhibition of farnesyl transferase by scintillation proximity assay (SPA)

The principle of the SPA technology (H. E. Hart and E. B. Greenwald, J. Nucl Med, 20, 1062–1065, 1979 and Nelson N., Analytical Biochemistry, 165, 287–293, 1987) is applied to the assay of the enzymatic activity of farnesyl transferase (Ftase). This enzyme has been partially purified from human THP1 cells (Fromage N., Guitton J. D., Joyeux C., Desanlis F., Boniface O., Soria H. M., Boucher F., Clerc F. F., Crespo A., Duchesne M., Lavayre J., Tocque B;, Van Der Pyl D., Mayaux J. F., Becquart J., 5th European Meeting of GFBC on bio-chromatography and molecular biology, May 12–14, 1992, France). The biotinylated acceptor substrate is a peptide of 11 amino acids corresponding to the terminal sequence of lamin B (BLB). The donor substrate, farnesyl pyrophosphate, is labelled with tritium $^3$H FPP. The enzyme transfers the $^3$H FPP to the biotinylated acceptor substrate and once the reaction has stopped, the farnesylated peptide is captured by beads encapsulating a fluorescent scintillant and which are coupled to streptavidin (Amersham kit, TRKQ7010®). The radiolabelled peptide excites the beads which then emit light which is quantified in a solid-liquid scintillation counter (Topcount®, Packard).

The SPA reaction is started by adding 40 $\mu$l of Ftase (2 $\mu$g) to a microplate containing 20 $\mu$l of BLB (0.1 $\mu$M), 20 $\mu$l of $^3$H FPP (0.12 $\mu$M) and 20 $\mu$l of assay buffer 50 mM Hepes, pH 7.5, 5 mM MgCl$_2$, 5 mM DTT, 20 mM KCl, 0.01% triton X100 (control) or 20 $\mu$l of sample diluted in the assay buffer (screening). The plate is incubated for 60 minutes at 37° C. and the reaction is stopped by adding 150 $\mu$l of stopping reagent containing the SPA beads. The plate is sealed with an adhesive film and left for 30 minutes at room temperature in order to reach equilibrium, and then counted in the Topcount counter. The results are counted as disintegration per minute, dpm, and expressed in % inhibition relative to the enzyme control (after subtracting the blank). The IC50 values of the compounds are calculated by nonlinear regression.

EXAMPLE 1

Preparation of an Active Metabolite According to the Invention from the Chrysosporium strain CBS 123.95.

Three 250 ml Erlenmeyer flasks filled with 50 ml of previously sterilized medium (peptone 5 g/l, meat extract 5 g/l, glucose 10 g/l, sodium chloride 5 g/l, agar 1 g/l, tween-85 1 g/l, pH 7.2) are inoculated with a Chrysosporium culture CBS 123.95 in the form of a frozen liquid culture. They are stirred at 240 rpm in a shaker thermostatted at 28° C.

After 5 days, 100 ml of these cultures are transferred into a 6 l round-bottomed flask filled with 2 l of the same medium. This round-bottomed flask, provided with two side tubes (one for seeding, the other for inoculating the fermenter) is stirred at 22° C. on a magnetic drum at about 600 revolutions per minute. After incubating for 72 hours, the whole of this culture is transferred under sterile conditions into a 100 liter production fermenter filled with 60 liters of previously sterilized medium (malt extract 20 g/l, agar 1 g/l, Tween-85 1 g/l). For 142 hours, the culture is kept at a temperature of 23° C., a pressure of 0.5 bar, stirred at 200 rpm and aerated at the rate of 1.5 m³/h.

Extraction and Purification 58.2 kg of broth are acidified to pH 3 and then stirred for 1 hour with 1 volume of ethyl acetate. After separating the organic phase by centrifugation, the whole of the preceding operations is repeated once. The 2 organic phases are combined and concentrated under reduced pressure to 5 liters. The ethyl acetate extract obtained is extracted in turn by stirring for one hour with 1 volume of an aqueous solution alkalized to pH 9. The organic phase is removed by decantation and centrifugation. The aqueous phase is acidified to pH 3 and extracted with twice 1 volume of ethyl acetate. After decantation and centrifugation, the organic phase is concentrated under reduced pressure to 1.5 liters; at this stage of concentration, a precipitate appears. After decantation, the supernatant is removed and the precipitate formed is separated by filtration on No. 4 sintered glass. After drying overnight in a vacuum oven, a 1.7 g extract is obtained having an $IC_{50}$ of less than 3 $\mu$g/ml.

The next purification stage consists in a permeation chromatography on a Sephadex LH20® support (Pharmacia), carried out on aliquot portions of this dry extract. For example, 500 mg are dissolved in 10 ml of a 1/1 v/v MeOH/$H_2O$ mixture and then deposited at the top of a cylindrical glass column with an internal diameter of 30 mm and a height of 100 cm containing the support previously swollen in methanol. The elution is carried out in methanol at 0.5 ml/min. 2 ml fractions are collected. At this stage, the fractions obtained can be analysed by thin-layer chromatography on a Merck 60 F 254® silica plate with the eluent AcOEt/EtOH/$H_2O$ 40:15:15, v:v:v. In this system, the desired metabolite migrates with a retardation factor (Rf) of between 0.4 and 0.50, and comes out blue in colour after spraying with the Dittmer reagent (Sigma molybdenum blue ®). The active metabolite is located in fractions 25 to 45 which are pooled, evaporated under vacuum to give in total 1.1 g of beige powder exhibiting an $IC_{50}$ of less than 1 $\mu$g/ml.

The purification may be continued by high-performance liquid chromatography: the preceding active product (1.1 g), resuspended in a 50:50 MeOH/$H_2O$ mixture, is injected at the rate of 0.5 ml for each chromatography into an HPLC apparatus equipped as follows:
column: BioSil EL90-10® (Biorad), $C_{18}$ 10 $\mu$m, 250×10 mm
flow rate of 3 ml/min isocratic elution A/B, 20:80, v:v A: $H_2O$ with 0.1% TFA B: $CH_3CH/H_2O$, 95:5, with 0.1% TFA UV detection at 210 nm.

The active metabolite is collected at the retention time of 6.6 min. At the end of multiple injections and separations by HPLC under the abovementioned conditions, the fractions containing the active product are combined. After evaporation of the acetonitrile under reduced pressure, the active extract is percolated on a Varian $C_{18}$ Mega Bond Elut® column which is then rinsed with distilled water until the pH of the eluent becomes neutral; the elution is then carried out with about 20 ml of methanol. After evaporation of the methanolic eluate under reduced pressure, 1 g of light beige powder is obtained which corresponds to the following active metabolite

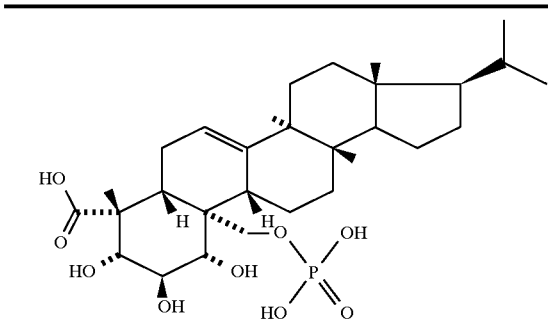

Physicochemical properties

| Molecular formula | $C_{30}H_{49}O_9P$ |
|---|---|
| M.S (m/z) | 583 (M−H) |

NMR characterization of this compound in DMSO-$d_6$ (T=300K)

| Position No. | δc (150 MHz) | δu (600 MHz) |
|---|---|---|
| 1 | 82 | 2.98 (1H, d, 6Hz) |
| 2 | 74 | 3.70 (1H, t, 7Hz) |
| 3 | 77.5 | 3.50 (1H, d, 7Hz) |
| 4 | 52.7 | |
| 4a | 47 | 2.05 (1H, m) |
| 5 | 27 | 2.10 (1H, m) |
|  |  | 1.77 (1H, m) |
| 6 | 117 | 5.28 (1H, m) |
| 6a | 147 | |
| 6b | 42.6 | |
| 7 | 31.3 | 1.35 (1H, m) |
|  |  | 1.50 (1H, m) |
| 8 | 37 | 1.64 (1H, m) |
|  |  | 1.40 (1H, m) |
| 8a | 43.5 | |
| 9 | 60 | 0.94 (1H, m) |
| 10 | 29 | 1.15 (1H, m) |
|  |  | 1.74 (1H, m) |
| 11 | 20.7 | 1.20 (1H, m) |
|  |  | 1.35 (1H, m) |

-continued

| Position No. | δc (150 MHz) | δu (600 MHz) |
|---|---|---|
| 11a | 55 | 1.35 (1H, m) |
| 11b | 36.3 | |
| 12 | 33.7 | 1.29 (2H, t, 3Hz) |
| 13 | 20.7 | 2.19 (1H, m) |
| | | 1.75 (1H, m) |
| 13a | 50.5 | 2.63 (1H, m) |
| 13b | 45.7 | |
| 14 | 180 | |
| 15 | 11.8 | 1.17 (3H, s) |
| 16 | 25 | 0.99 (3H, s) |
| 17 | 15 | 0.67 (3H, s) |
| 18 | 31.4 | 1.40 (3, m) |
| 19 | 23 | 0.83 (3H, d, 6Hz) |
| 20 | 24 | 0.79 (3H, d, 6Hz) |
| 21 | 22 | 0.81 (3H, s) |
| 22 | 60.5 | 3.60 (1H, d, 6Hz) |
| | | 4.02 (1H, t, 6Hz) |

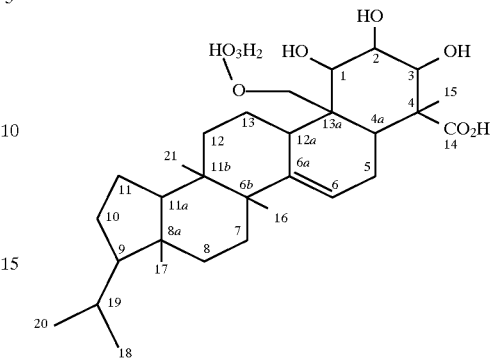

EXAMPLE 2
Determination of the Farnesyl Transferase Protein Inhibiting Activity This activity is assessed for the metabolite of Example 1 according to the method described in the preceding section entitled Materials and Methods.

| | CVFM* | 1 |
|---|---|---|
| $IC_{50}$ | 52 nM | 830 nM |

*Peptide (cysteine-valine-phenylalanine-methionine) used as control in the measurement of farnesyl transferase activity.

---

We claim:
1. A compound of the general formula I

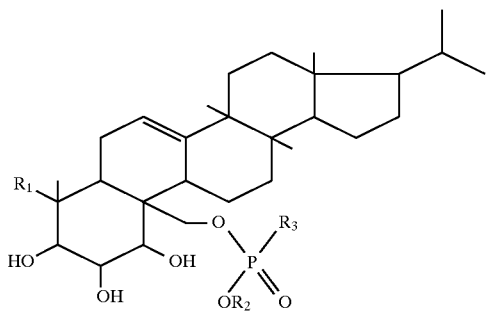

in which:
R$_1$ represents a C$_1$ to C$_5$ alkoxy group, an aldehyde group, a carboxyl group, a C$_1$ to C$_5$ alkyl ester or a (C$_1$ to C$_5$ alkyl)hydroxyl group,
R$_2$ represents a hydrogen atom or a C$_1$ to C$_4$, linear or branched, lower alkyl group, and
R$_3$ represents a C$_1$ to C$_4$ alkyl group, a hydroxyl group or a C$_1$ to C$_4$ alkoxy group,
or salt thereof.

2. A pharmaceutical composition comprising a pharmaceutically sufficient amount of the compound according to claim 1, or a slat thereof, or physiologically active pharmaceutically acceptable adjuvants.

3. A method for treating a mammal subject to having normal cells therein transformed into cancerous cells by administering to the mammal a farnesyl transferase inhibitory amount of the compound according to claim 1, or a pharmaceutically acceptable salt thereof.

4. A process for preparing the compound according to claim 1 comprising culturing Chrysosporium strain No. CBS 123.95, or mutant thereof, or derivative thereof, in a culture medium, and recovering by extraction from the culture medium the compound.

5. A method for treating or preventing cancer, comprising adminstering to a patient a therapeutically effective dose of a compound according to claim 1, or a pharmaceutically acceptable salt thereof.

6. A method for treating or preventing cancer caused by modified ras protein in a patient comprising adminstering to the patient a therapeutically effective dose of a compound according to claim 1, or a pharmaceutically acceptable salt thereof.

7. A method for a therapy, wherein the therapy involves the inhibition of farnesyl transferase in a patient, comprising administering to the patient a therapeutically effective amount of a compound according to claim 1 or a pharmaceutically acceptable salt thereof.

8. A method of inhibiting farnesyl transferase activity comprising combining a sufficient quantity of the compound of formula I to effect inhibition of farnesyl transferase activity, with a composition containing farnesyl transferase.

9. A compound of the general formula II:

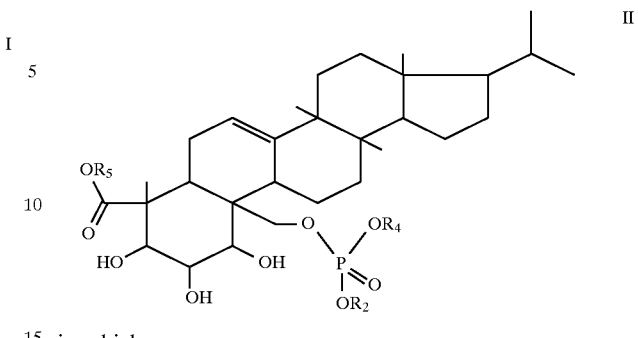

in which:
R$_2$ and R$_4$ represent, independently of each other, a hydrogen atom or a C$_1$ to C$_4$, linear or branched, lower alkyl group, and
R$_5$ represents a hydrogen atom, a C$_1$ to C$_5$ alkyl group, where appropriate substituted with a group chosen from the hydroxyl or phenyl groups, optionally substituted with one or more methyl, methoxy, hydroxyl or halogen groups, or salt thereof.

10. A compound of formula

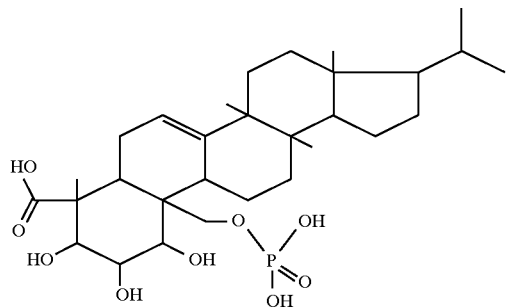

or salt thereof.

11. A compound according to claim 10 of the formula

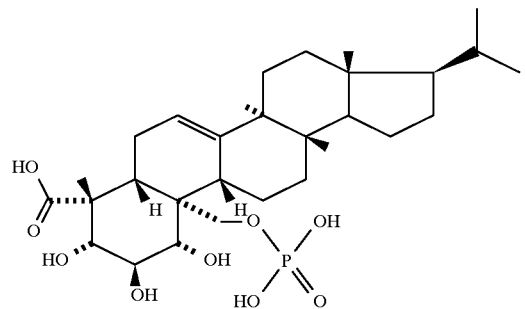

or a salt thereof.

12. Chrysosporium strain No. CBS 123.95 or mutant thereof or derivative thereof.

* * * * *